Figure 1:
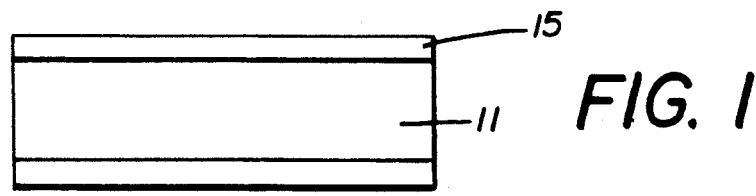

United States Patent
Pollack

[11] Patent Number: 5,182,791
[45] Date of Patent: Jan. 26, 1993

[54] PROBE FOR TRANSMITTING LIGHT THROUGH A FLUID

[76] Inventor: Michael J. Pollack, 2089 N. Line St., Lansdale, Pa. 19446

[21] Appl. No.: 739,093

[22] Filed: Aug. 1, 1991

[51] Int. Cl.$^5$ .............................................. G02B 6/00
[52] U.S. Cl. ..................................... 385/147; 385/141
[58] Field of Search ..................... 385/147, 31, 24, 33, 385/47, 51, 71, 141

[56] References Cited

U.S. PATENT DOCUMENTS

| 4,834,497 | 5/1989 | Angel | 385/31 X |
| 4,988,163 | 1/1991 | Cohen et al. | 385/31 |
| 5,061,026 | 10/1991 | Clarke et al. | 385/147 X |

Primary Examiner—John D. Lee
Assistant Examiner—Phan Thi Heartney
Attorney, Agent, or Firm—William E. Cleaver

[57] ABSTRACT

The present device is a light transmission probe which is designed to transmit light through a fluid, which is held by a tank or in a pipe or the like. By analyzing the change in amplitude and/or frequency of the light transmitted, certain parameters of the fluid can be determined. The present light transmission probe, in a preferred embodiment, includes a sapphire rod or window as the light conducting medium. Further, in a preferred embodiment, the sapphire rod has a layer of titanium molymanganese metallized to its lengthwise surface and the metallized larger is fused to the inside cylindrical aperture of a stainless steel housing. The combination just described provides a probe which does not react to the presence of chemicals normally used in the chemical industry and can withstand relatively high pressures and relatively high temperatures.

8 Claims, 1 Drawing Sheet

PROBE FOR TRANSMITTING LIGHT THROUGH A FLUID

BACKGROUND OF THE DISCLOSURE

In the chemical industry and in particular that part of the chemical industry which deals with fluids packaged in tanks, or fluids passing through pipes, it has become the practice to determine the physical, or chemical spectra, and/or other characteristics of such fluids by passing light energy through the fluids. The loss of light energy, or a change in frequency of such light energy, provides evidentiary data, which enable the user to determine certain sought after parameters. In such arrangements, there is generally a transmitter probe and a receiving probe or multiples thereof. The probes are secured to the side of the tank, or on a pipe, or on a fluid container of some sort. A probe is not simply secured to the tank, or pipe, or fluid container, but has an end which enters the tank, or the like, to come in contact with the fluid, in order to transmit the light energy through the fluid. In the prior art, the probes have been made using a housing of stainless steel with a hollowed out cylinder formed therein. Into the hollowed out cylinder there is inserted a bundle of fiberglass optics. In the prior art, the bundle of fiberglass optics is secured to the stainless steel housing by an epoxy glue or mechanical interference fit or crimp. There are a number of problems with the prior art probes. For instance, when one of the prior art probes is located in a tank, and there is a great deal of fluid pressure against that probe a problem often develops. In response to the fluid pressure (in the foregoing situation) there is a "push" against the fiberglass optics which acts to "push" the fiberglass optics into the stainless steel housing, (i.e. out of the tank), thereby causing the probe to leak. In such cases it has been found that the epoxy glue has a strong affinity for the stainless steel but does not have a strong affinity for the bundle of fiberglass optics. Very often, in such cases, a tunnel, or a hollowed out cylinder, is formed in the epoxy glue and it is apparent that in the prior art the epoxy glue does not always hold the fiberglass optics against fluid pressure. Another problem, with the fiberglass optics arrangement, is that the glass does not give satisfactory transmission of light energy at certain frequencies. In addition fiberglass optics are susceptible to damage from certain fluid materials such as acids and the like. In this last mentioned regard it is true that a bundle of fiber optics provides voids (spaces between the fiber optics) which enable the fluids to enter into the bundle and do damage. Mechanical interference fit, or crimping, and/or epoxy application to windows in front of the fiber optics bundle were tried in order to minimize corrosion and pressure effects on fibers. However the probes formed by these methods are very limited because they leak at relatively low pressure. The present structure overcomes the infirmaties of the prior art light transmission probes.

SUMMARY OF THE INVENTION

The present probe, in a preferred embodiment, is composed of a sapphire rod or a window held in a stainless steel housing. While sapphire rods or windows are employed in both the transmitting probe and the receiving probe, in a preferred embodiment, it should be understand that quartz rods or windows could be used. Both sapphire rods and quartz rods are normally not susceptible to chemical reactions. In addition, both sapphire rods and quartz rods can be secured to stainless by first metallizing the rods with titanium molymanganese or some other active metal alloy. The titanium molymanganese is screened, or brushed on the surface of the rod and thereafter the rod is "fired" in a vacuum furnace. After the metallized material has been fired onto the rod surface, the coated rod is inserted into the cylindrically shaped aperture in the stainless steel housing. Then the gap between coating on the rod and the inside of the cylindrically shaped aperture of the stainless steel housing is measured and the proper amount of brazing material is inserted into the gap. The gap is usually about 2 to 4 thousandths of an inch wide and since the density of the brasing material is known, mathematically the proper amount of brazing material can be determined and is inserted into the gap. In a preferred embodiment about 25% more brazing material is employed, than the calculations call for, to provide beads of the material at the edge of the gap. Such an arrangment can withstand 7500 PSI of fluid pressure and will not be adversely affected by temperatures up to 700 degrees centigrade. In a second embodiment sapphire rods and/or quartz rods are brushed or coated with ceramic glass material paste, and thereafter the rod is inserted into the stainless steel housing and fired. In the second embodiment the ceramic glass paste is fused directly to the rod and directly to the stainless steel during the firing. The rod is thus secured to the housing. In the second embodiment when the ceramic glass composition paste is brushed onto the rod it is done so to a thickness of 20 to 30 thousandths of an inch. The second embodiment can withstand fluid pressures of up to 5000 PSI and such rods are not adversely affected by temperatures up to 600 degrees centigrade. A third embodiment for securing the sapphire rods and/or quartz rods to a housing involves a preform of ceramic glass material around the rod and then inserting the rod into a stainless steel housing. Thereafter the package is fired and the ceramic glass material preform under pressure at softening temperature will fuse to the sapphire rod as well as to the housing.

Figure 2:
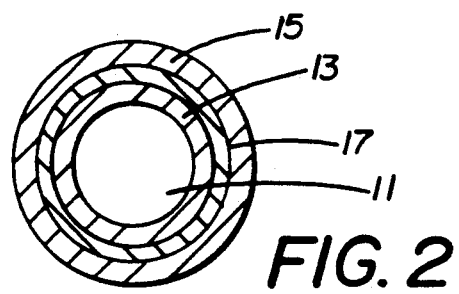
Figure 3:
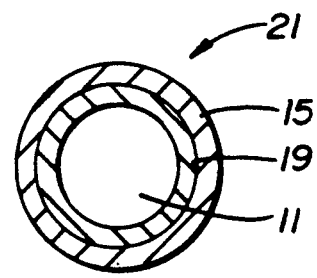
Figure 4:
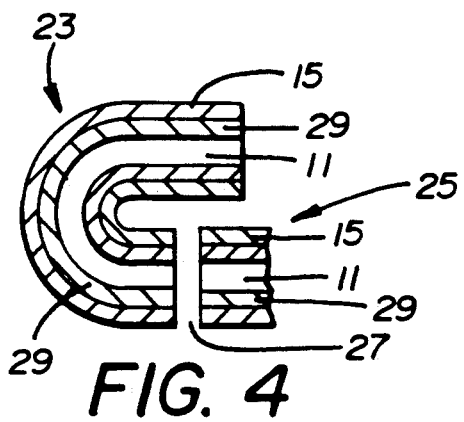
Figure 5:
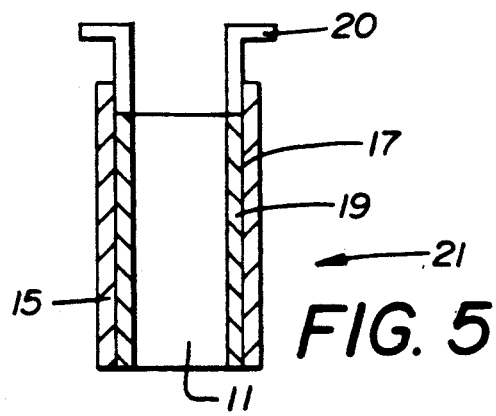

The objects and features of the present invention will be better understood in view of the following description taken in conjunction with the drawings wherein:

FIG. 1—Depicts a sapphire rod with a metallized coating thereon;

FIG. 2—Is an end view of a sapphire rod with a metallized coating and with a layer of brazing material on the metallized coating and with the package inserted into a stainless steel housing;

FIG. 3—Depicts a sapphire rod coated with either glass ceramic material, or paste with ceramic material therein, each of which is inserted into a stainless steel housing;

FIG. 4—Depicts a rod with an arcuately shaped arrangement showing the utility of ceramic paste; and FIG. 5—Shows a ceramic glass preform between a sapphire rod with a piston applying preserve to the preform.

Figure 6:
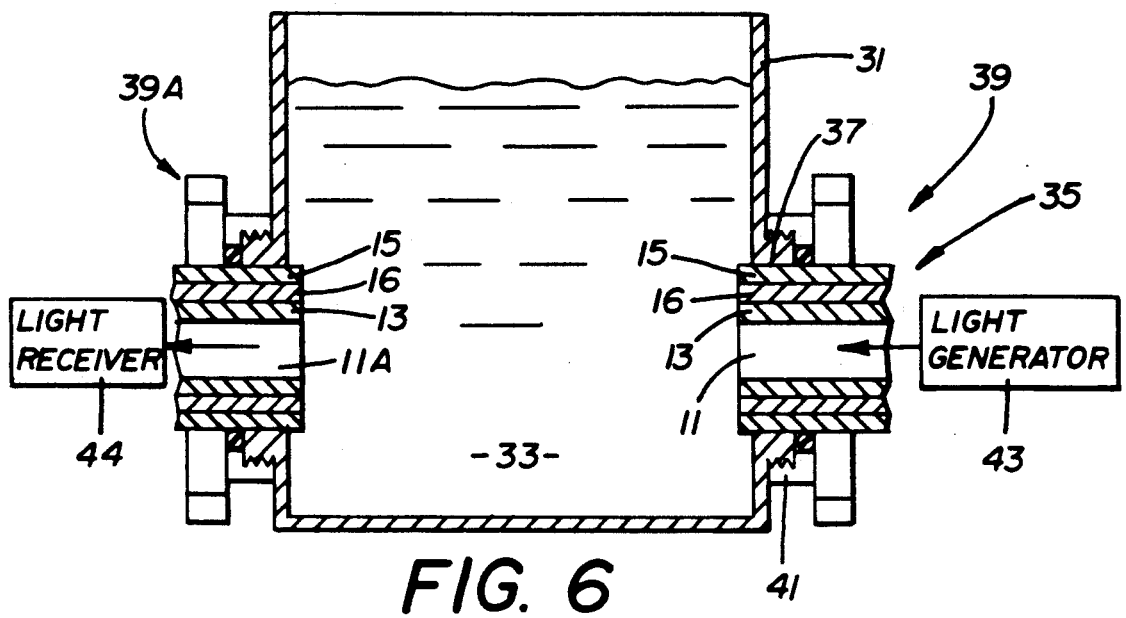

FIG. 6—Shows a tank with fluid therein and a light transmitting probe and a light receiving probe.

Consider FIG. 1

In FIG. there is shown a sapphire rod which is employed in a preferred embodiment. Although the description throughout refers to a sapphire rod, it should be understood that a quartz rod can be employed. Some other material may be used if such other material exhibits good ability to transmit light energy without amplitude, or frequency, distortion; a good ability to resist reacting to chemicals used in the chemical industry; and an ability to be fabricated, or formed, in a voidless form, i.e. a solid piece without voids formed therein.

In a preferred embodiment, the sapphire rod 11 has a layer of titanium-molymanganese 13 secured thereto. The layer of titanium-molymanganese 13 is brushed on, or screened onto, the lengthwise surface of the sapphire rod 11. Thereafter, the rod is "fired" in a vacuum furnace at a temperature in the range of 1300 degrees centigrade to 1600 degrees centigrade. After the rod 11 is metallized with the fired layer of titanium-molymanganese secured thereto, it is inserted into a cylindrically shaped aperture formed within the stainless steel housing 15. When the metallized rod 11 is located in the stainless steel housing 15, there remains a gap 17. The gap 17 is filled, or loaded, with brazing material such as an alloy of gold/nickel, and then the package is fired. The gap 17 is usually 2 to 4 thousandths of an inch wide. Since the width of the gap is known, and the periphery of the gap is known, and the length of the rod is known, the volume to be filled by the brazing material can be mathematically determined. Further, since the density of the brazing material is known, the amount of the brazing material required to fill the gap 17 can be determined mathematically. As was mentioned above, the gap is filled with the proper amount of brazing material plus 25% more than the calculations indicate. As mentioned in the summary, the additional 25% enables the technique to provide beads of material at the edge of the gap which is very useful. In response to the metallized rod 11 (with the gap loaded with the brazing material) being fired with the stainless steel housing 15, the brazing material fuses with both the stainless steel housing and with the titanium molymanganese coated rod to form a solid probe. The probe whose formation was just described above, can withstand fluid pressures of up to 7500 PSI and will experience no ill effects from fluid temperatures up to 700 degrees centigrade. Since both the sapphire rod and/or quartz rod do not react to chemicals of the kind normally employed in the chemical industry, the probe described above, is a very desirable probe for the chemical industry.

While we have described employing titanium molymanganese as the metallizing material, it should be understood that other metallic materials such as gold titanium, molymanganese glass frit, and molymanganese zirconium could be employed within the spirit of the present invention.

In a second embodiment, the rod 11 is not initially metallized as was done in the first embodiment described above. In the second embodiment, the rod 11 is layered with ceramic glass material paste. The rod layered with the glass ceramic material paste is inserted into the cylindrically shaped aperture in the stainless steel housing. During such a process some of the ceramic glass paste brushes off, or falls off, and therefore, some ceramic glass paste or preform is loaded into, or packed into, the gap between the inserted rod Il and stainless steel housing. It follows that the stainless steel housing 15, the packed ceramic glass paste 19 and the rod Il (see FIG. 3 and 5) form a solid package 21. The layer of glass ceramic material is generally in the range of 20 to 30 thousandths of an inch. The package 21 is "fired" in a vacuum furnace (or in a reducing environment) at temperatures of 900° C. to 1100° C. The ceramic glass paste fuses to both the stainless steel housing 15 and the rod 11. The affinity of the fused glass material for the stainless steel housing and for the sapphire rod is not as great as the brazing material for the metallized surface 19 in the stainless steel housing 15 as described with respect to the first embodiment. Accordingly, we find that the second embodiment will withstand 5,000 PSI of fluid pressure and there will be no ill effects up to 600 degrees centigrade. The upside with the use of the second embodiment, as compared with the use of the first embodiment, is that the second embodiment is less expensive to fabricate than was the first embodiment. Hence if the application (where the probe is to used) does not require greater limits than 5,000 PSI and 600 degrees centigrade, then it would seem that the second embodiment would be more attractive. In addition the paste can be used to accommodate irregular geometric such as shown in FIG. 4. In FIG. 4, the sapphire rod 11 represents a transmitting probe at station 23 and a receiving probe at station 25. The fluid that is being monitored passe through the gap 27. The stainless steel housing 15 is slipped on sideways in two sections. The ceramic glass paste after firing is shown by the layer 29.

A third embodiment involves employing a preform of ceramic glass material which is placed around the rod. Thereafter, the rod 11 with the preform located around the rod is placed in the stainless steel housing. The package is fired at temperatures of 900° C. to 1100° C. in a vacuum furnace with a piston pushing the preform into the housing to fill the gap between the housing and the rod, (or a reducing environment) and the ceramic glass material in the preform is fused to both the sapphire rod and the stainless steel housing 15. However, as was true with the second embodiment, if the application of the probe does not require the probe to withstand fluid pressures in excess of 5000 PSI, or does not require that the probe avoid being subjected to temperatures higher than 600 degrees centigrade, then the third embodiment could be attractive from an economic standpoint.

FIG. 5 depicts a probe with the third embodiment arrangement. In FIG. 5 there is shown a rod 11, a stainless steel housing 15 and a preform 19 being pushed by the piston 20 into the gap 17.

In FIG. 6 there is shown a tank, or fluid carrier means 31, holding a fluid 33. The user is interested in determining the viscosity of the fluid 33. A transmitting probe 35 is fitted into the carrier 31, through the aperture 37, as shown. The securing means 39 (which is a threaded nut) has a threaded section 41 which threads into the carrier 31. The transmitting probe 35 is shown in section to depict the sapphire rod 11, the metallized titanium molymanganese 13, the brazing material 16 and the stainless steel housing 15. Coupled to the sapphire rod 11, is a light generator 43. The light generator 43 transmits light energy through the sapphire rod 11. The light energy is transmitted through the fluid 33 and changes in both amplitude and frequency in accordance with the density, or viscosity, of the fluid. The altered light energy is received by the receiving sapphire rod 11A. The receiving package is fabricated in the same fashion as was the transmitting probe with the layer of titanium molymanganese 13, the layer of brasing material 16, and the stainless steel housing 15. The receiving probe is secured by a threaded nut 39A. Coupled to the sapphire rod 11A is light receiving circuitry 44 which amplifies the signals and then transmits them to a data processor to determine the viscosity (or other parameters).

I claim:

1. A probe for transmitting light through a fluid which is disposed in a carrier means, which carrier means has an aperture therein, comprising in combination:

voidless rod means, which is formed to pass light energy with relatively little distortion with respect to amplitude and frequency;

metal housing means, with an aperture therethrough and with said voidless rod disposed in said aperture;

fusing means, disposed between said voidless rod and said metal housing means, said fusing means being fired to fuse said fusing means, to both said metal housing means and said voidless rod, whereby said voidless rod is held firmly within said metal housing means; and securing means, secured to said metal housing means and formed to be secured to said carrier means to dispose at least a part of said voidless rod through said aperture in said carrier means to come in contact with said fluid held by said carrier means.

2. A light transmission probe according to claim 1 wherein said voidless rod is a rod formed of sapphire.

3. A light transmission probe according to claim 1 wherein said voidless rod is a rod formed of quartz.

4. A light transmission probe according to claim 1 wherein said metal housing means is fabricated from stainless steel.

5. A light transmission probe according to claim 2, wherein said fusing means is a ceramic glass material.

6. A light transmission probe according to claim 2, wherein said fusing material is a paste of ceramic material.

7. A light transmission probe for transmitting light through a fluid which is disposed in a carrier means, which carrier means has an aperture therein, comprising in combination:

voidless rod means, formed of sapphire which is formed to pass light energy with relatively little distortion with respect to amplitude and frequency;

metal housing means, with an aperture therethrough and with said voidless rod disposed in said aperture;

fusing means, disposed between said voidless rod and said metal housing means, said fusing means being fired to fuse said fusing means, to both said metal housing means and said voidless rod, whereby said voidless rod is held firmly within said metal housing means; and securing means, secured to said metal housing means and formed to be secured to said carrier means to dispose at least a part of said voidless rod through said aperture in said carrier means to come in contact with said fluid held by said carrier means.

8. A light transmission probe according to claim 7, wherein said metal housing means is fabricated from stainless steel.

* * * * *